(12) United States Patent
Campbell et al.

(10) Patent No.: US 11,420,048 B2
(45) Date of Patent: Aug. 23, 2022

(54) SKIN REJUVENATION DEVICE

(71) Applicant: HER Technologies, INC., Dallas, TX (US)

(72) Inventors: Mark Campbell, Grand Rapids, MI (US); Thomas Murphy, Frisco, TX (US)

(73) Assignee: HER TECHNOLOGIES INC., Dallas, TX (US)

( * ) Notice: Subject to any disclaimer, the term of this patent is extended or adjusted under 35 U.S.C. 154(b) by 81 days.

(21) Appl. No.: 16/643,382

(22) PCT Filed: Aug. 30, 2018

(86) PCT No.: PCT/IB2018/056649
§ 371 (c)(1),
(2) Date: Feb. 28, 2020

(87) PCT Pub. No.: WO2019/043628
PCT Pub. Date: Mar. 7, 2019

(65) Prior Publication Data
US 2021/0069502 A1 Mar. 11, 2021

Related U.S. Application Data

(60) Provisional application No. 62/553,372, filed on Sep. 1, 2017.

(51) Int. Cl.
*A61N 1/32* (2006.01)
*A61N 1/36* (2006.01)
(Continued)

(52) U.S. Cl.
CPC ......... *A61N 1/328* (2013.01); *A61N 1/0472* (2013.01); *A61N 1/36034* (2017.08); *H02J 7/007* (2013.01); *H02J 2207/20* (2020.01)

(58) Field of Classification Search
CPC .... A61N 1/0472; A61N 1/0476; A61N 1/328; A61N 1/3603; A61N 1/36034; H02J 7/007; H02J 2207/20
(Continued)

(56) References Cited

U.S. PATENT DOCUMENTS

| 8,954,155 B2 | 2/2015 | Campbell | |
| 2004/0230227 A1* | 11/2004 | Avrahami | ................ A61N 1/30 607/3 |

(Continued)

OTHER PUBLICATIONS

International Search Report and Written Opinion of the International Searching Authority from corresponding Patent Cooperation Treaty (PCT) Application No. PCT/IB2018/056649, indicated completed on Dec. 7, 2018.

(Continued)

*Primary Examiner* — Carl H Layno
*Assistant Examiner* — Jane C Kalinock
(74) *Attorney, Agent, or Firm* — Gardner Linn

(57) ABSTRACT

A device and method for rejuvenating skin includes a power supply adapted to generate a voltage and an applicator. The applicator includes a first node and a second node, wherein the first node is adapted to be configurable between a positive electrode or electrically isolated from the power supply, and wherein the second node is adapted to be configurable between a negative electrode or electrically isolated from the power supply. The power supply delivers a current through the first node when the first node is configured as the positive electrode and current returns to the power supply through the second node when the second node is configured to be the negative electrode.

19 Claims, 5 Drawing Sheets

(51) Int. Cl.
*A61N 1/04* (2006.01)
*H02J 7/00* (2006.01)

(58) Field of Classification Search
USPC .......................................... 607/59
See application file for complete search history.

(56) References Cited

U.S. PATENT DOCUMENTS

| | | |
|---|---|---|
| 2006/0253165 A1 | 11/2006 | O'Kelly |
| 2010/0274329 A1 | 10/2010 | Bradley et al. |
| 2013/0103118 A1 | 4/2013 | Magee |
| 2014/0324135 A1 | 10/2014 | Jones |
| 2014/0343625 A1* | 11/2014 | O Laighin ......... A61N 1/36034 607/48 |
| 2016/0151238 A1* | 6/2016 | Crunick ............. A61H 23/0218 601/2 |
| 2016/0346530 A1 | 12/2016 | Jeffrey et al. |

OTHER PUBLICATIONS

Preliminary Report on Patentability of the International Searching Authority from corresponding Patent Cooperation Treaty (PCT) Application No. PCT/IB2018/056649, completed Mar. 3, 2020.

* cited by examiner

SKIN REJUVENATION DEVICE

CROSS-REFERENCES TO RELATED APPLICATIONS

The present application is a § 371 national stage of International Application PCT/IB2018/056649, filed Aug. 30, 2018, which claims benefit of U.S. Provisional Application No. 62/553,372, filed on Sep. 1, 2017, both of which are hereby incorporated herein by references in their entireties.

BACKGROUND OF THE INVENTION

The present invention is directed to an apparatus and method for improving the condition of skin. In particular, the apparatus and method are directed towards applying electrical stimulation to skin to reduce the effects of aging.

SUMMARY OF THE INVENTION

Anti-aging dermatological treatments to improve the appearance of aging of skin are prevalent. Some methods include providing electrical stimulation directly to the affected skin. However, the desires and goals of the user and conditions of the skin can greatly affect the characteristics of the optimal electrical signal to provide to the tissue. The present invention provides the benefit of allowing a single skin rejuvenation device to provide a wide variety of electrical stimulation to the skin.

A skin rejuvenation device, in one aspect of the invention, includes a power supply adapted to generate a voltage. The device also includes an applicator. The applicator includes a first node and a second node, wherein the first node is adapted to be configurable between a positive electrode electrically coupled to the power supply or electrically isolated from the power supply. The second node is adapted to be configurable between a negative electrode electrically coupled to the power supply or electrically isolated from the power supply. The power supply delivers a current through the first node when the first node is configured as the positive electrode and current returns to the power supply through the second node when the second node is configured to be the negative electrode.

The device may also include a voltage control adapted to modulate a frequency of the voltage. The voltage control may modulate the frequency between 1,000 Hz and 350,000 Hz. The voltage control may also modulate at least one of amplitude, pulse rate, pulse sweep, and duty cycle of the voltage. The applicator may further include a convex surface, wherein the nodes are disposed on the convex surface. The power supply may be adapted to deliver a periodic voltage to the nodes. The periodic voltage may include a period of positive voltage followed by a period of no voltage. Additionally, the device may include a network interface or a wireless interface.

A skin rejuvenation device, in one aspect of the invention, includes a power supply adapted to generate a voltage. The device also includes an applicator. The applicator includes a plurality of nodes. Each node is adapted to be configurable between a positive electrode electrically coupled to the power supply, a negative electrode electrically coupled to the power supply, or electrically isolated from the power supply. The power supply delivers a current through each node configured as a positive electrode and current returns to the power supply through each node configured as a negative electrode.

The device may also include a voltage control adapted to modulate a frequency of the voltage. The voltage control may modulate the frequency between 1,000 Hz and 350,000 Hz. The voltage control may also modulate at least one of amplitude, pulse rate, pulse sweep, and duty cycle of the voltage. The applicator may further include a convex surface, wherein the nodes are disposed on the convex surface. The power supply may be adapted to deliver a periodic voltage to the nodes. The periodic voltage may include a period of positive voltage followed by a period of no voltage.

A skin rejuvenation device, in one aspect of the invention, includes a power supply adapted to generate a voltage. The device also includes an applicator. The applicator includes an applicator head. The applicator head includes a plurality of nodes. Each node is adapted to be a positive electrode electrically coupled to the power supply or a negative electrode electrically coupled to the power supply. The applicator head is adapted to be detachable from the adapter. The power supply delivers a current through each positive electrode and current returns to the power supply through each negative electrode.

The device may also include a voltage control adapted to modulate a frequency of the voltage. The voltage control may modulate the frequency between 1,000 Hz and 350,000 Hz. The voltage control may also modulate at least one of amplitude, pulse rate, pulse sweep, and duty cycle of the voltage. The applicator may further include a convex surface, wherein the nodes are disposed on the convex surface. The power supply may be adapted to deliver a periodic voltage to the nodes. The periodic voltage may include a period of positive voltage followed by a period of no voltage.

A skin rejuvenation device, in one aspect of the invention, includes a power supply adapted to generate a voltage. The power supply has at least one output terminal and provides a particular polarity between the output terminal and ground. The device also includes an applicator that includes a plurality of spaced apart electrically conductive nodes. The device also includes a control adapted to selectively connect each of the nodes with the output terminal of the power supply and selectively allow each of the nodes to float with respect to the output.

The control may also apply the output to at least one node to activate that node and not apply the output to at least one node to allow that node to float. The control may also allow that node to float and discharge that node. The control may also apply the output to at least one node to activate that node and allow that node to float to discharge that node. The output terminal may include at least two output terminals. The power supply may provide a particular polarity between one of the output terminals and ground and an opposite polarity between other output terminals and ground. The control may also be adapted to selectively connect each of the nodes with one of the output terminals and allow the other output terminals to float.

The plurality of nodes may include a plurality of first nodes, a plurality of second nodes, and a plurality of third nodes. At least some of the third nodes may be between one of the first nodes and one of the second nodes, and the control may be adapted to selectively connect the first nodes with one output terminal, the second nodes with the other output terminals, and the third nodes to float in order to define a first pattern where only the first and second nodes are activated. The control may be adapted to connect alternating ones of the electrodes with the one output terminal and the second output terminal to define a second pattern where all of the nodes are activated.

The device may also include a voltage control adapted to modulate a frequency of the voltage. The voltage control may modulate the frequency between 1,000 Hz and 350,000 Hz. The voltage control may also modulate at least one of amplitude, pulse rate, pulse sweep, and duty cycle of the voltage. The power supply may be adapted to deliver a periodic voltage to the nodes. The periodic voltage may include a period of positive voltage followed by a period of no voltage.

A method for stimulating skin with a device, in an aspect of the invention, includes stimulating skin with the device. The device includes a power supply adapted to generate a voltage. The device also includes an applicator. The applicator includes a plurality of nodes. Each node is adapted to be configurable between a positive electrode electrically coupled to the power supply, a negative electrode electrically coupled to the power supply, or electrically isolated from the power supply. The power supply delivers a current through each node configured as a positive electrode, and current returns to the power supply through each node configured as a negative electrode.

These and other objects, advantages and features of this invention will become apparent upon review of the following specification in conjunction with the drawings.

DETAILED DESCRIPTION OF THE PREFERRED EMBODIMENTS

Figure 1:
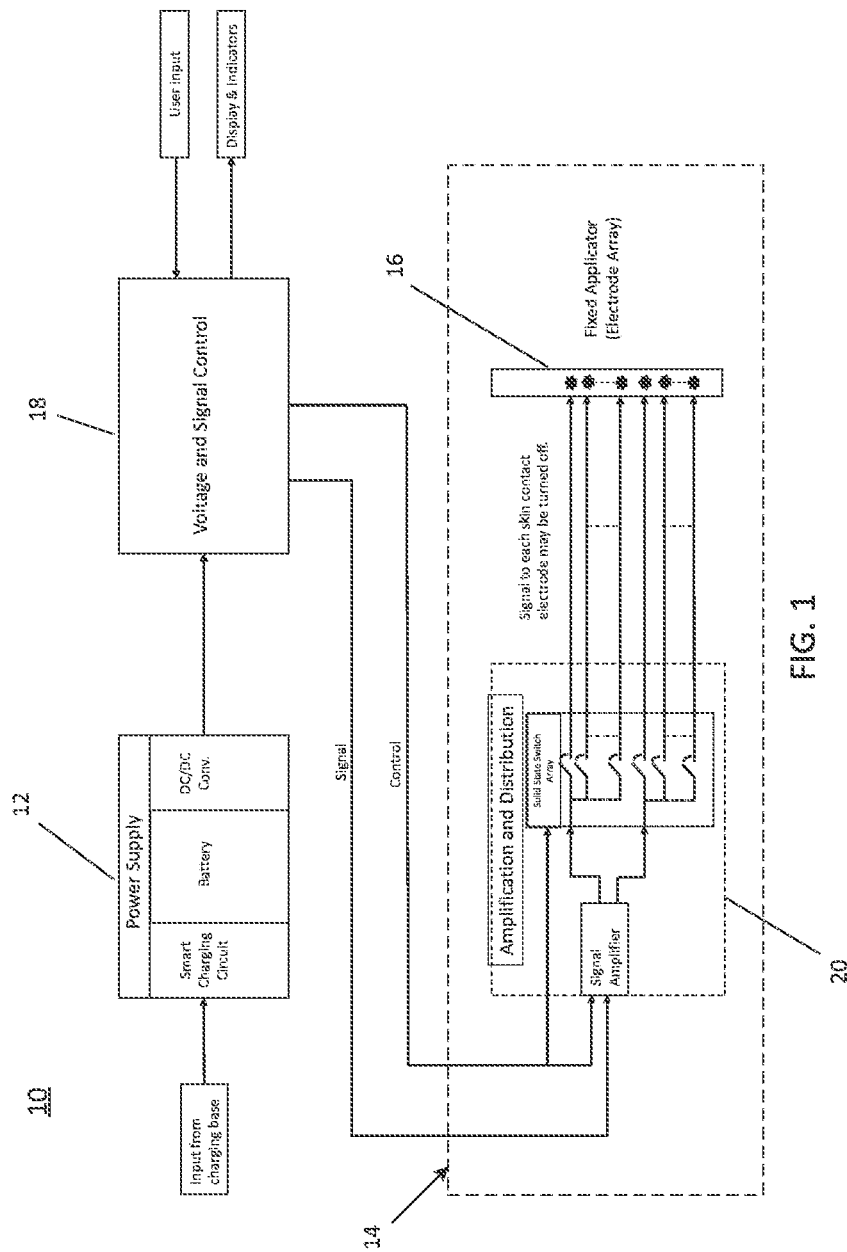
FIG. 1 is a block diagram of a skin rejuvenation device according to an embodiment of the invention.

Referring now to the drawings and the illustrative embodiment depicted therein, a device 10 to rejuvenate skin is disclosed. Further details of a skin rejuvenation device may be found in commonly assigned U.S. Pat. No. 8,954,155, entitled APPARATUS AND METHOD FOR REJUVENATING SKIN, the disclosure hereby incorporated herein in its entirety by reference. As shown in FIG. 1, the device 10 includes a power supply 12 that is adapted to generating a voltage. The device also includes an applicator 14. The applicator 14 is adapted to be pressed against or near the skin or tissue to be rejuvenated. The applicator 14 includes at least two nodes 16. A first node is adapted to be configurable between a positive electrode electrically coupled to the power supply 12 or electrically isolated from the power supply 12. A second node is adapted to be configurable between a negative electrode electrically coupled to the power supply 12 or electrically isolated from the power supply 12. The power supply 12 delivers a current through the first node when the first node is configured as the positive electrode, and current returns to the power supply through the second node when the second node is configured to be the negative electrode.

The power supply 12 is adapted to output a DC voltage. The power supply 12 may be adapted to accept a variety of voltage inputs. For example, the power supply 12 may be adapted to receive 110V AC voltage. The power supply may include a battery that is charged to provide power while the device 10 is not connected to an external voltage source. The power supply 12 may include a smart charging circuit to provide protection for the battery from charging and temperature. The power supply 12 may provide voltage conversion to provide the rest of the device 10 appropriate voltage. For example, the power supply may incorporate AC/DC conversion or DC/DC conversion.

Figure 5A:
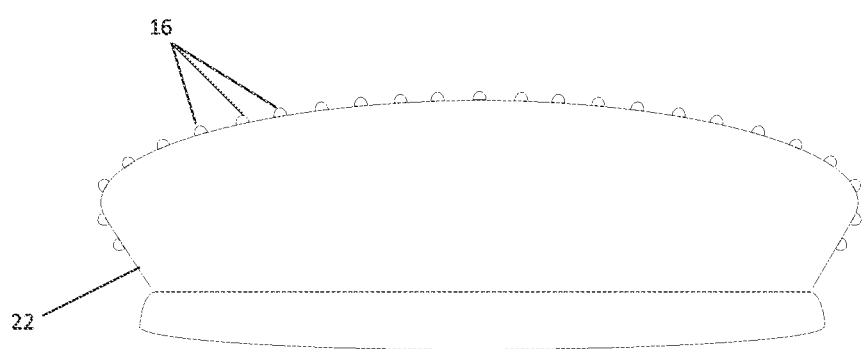
FIGS. 5A and 5B show alternate applicator head shapes according to an embodiment of the invention.
Figure 5B:
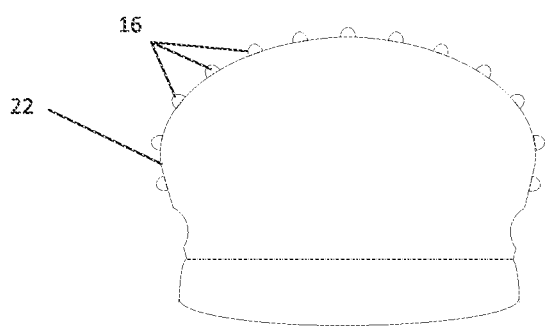

The device 10 also includes applicator 14 for a user to press to an area to be treated. The power supply 12 may be separate from the applicator 14, such that the power supply 12 provides power to the applicator 14 through a cord or wire. Alternatively, the power supply 12 may be integrated into the applicator 14, wherein the battery in the power supply 12 provides power to the applicator 14 while in use. The applicator may include an applicator head 22. The applicator head 22 includes the surface of the applicator that is applied to tissue. The surface may be a variety of shapes. For example, the surface may be flat. Alternatively, as shown in the illustrated embodiment of FIG. 5A and FIG. 5B, the surface may be convex. A convex surface facilitates contact with the various natural contours of the face, including, but not limited to, the naso-labial, periorbital, and glabellar frown areas. The applicator 14 or applicator head 22 includes a plurality of nodes 16 adapted to come in contact with skin or tissue to be treated.

Figure 4A:
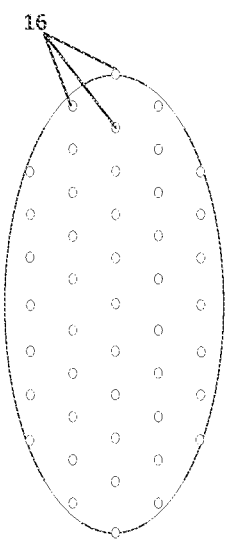
FIGS. 4A and 4B show alternate applicator nodes according to an embodiment of the invention.
Figure 4B:
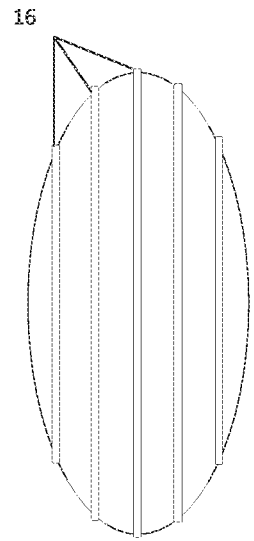

The nodes may be a variety of shapes. For example, in the illustrated embodiments of FIG. 4A and FIG. 4B, the nodes 16 are pin shaped, and blade shaped, respectively. However, other shapes are applicable. Each node is adapted to be configured in one of two states: coupled electrically to the power supply, or alternatively electrically isolated from the power supply. This state is commonly known as "floating." In such a state, no current is conducted through the node due to an external potential difference of a power source. At least one node 16 is configured to be either floating or a positive electrode. Hereinafter, a positive electrode refers to an electrode that may be configured between these two states. At least one node 16 is configured to be either floating or a negative electrode. Hereinafter, a negative electrode refers to an electrode that may be configured between these two states. When configured to be coupled electrically to the power supply 12, the positive electrodes conduct current provided by the power supply 12 to the skin. When configured to be coupled electrically to the power supply, the negative electrodes conduct current from the skin back to the power supply 12. In this way, current will flow from the power supply 12, through the positive electrode, through the skin to the negative electrode, and back to the power supply. When either type of node 16 is configured to be floating, the node will not conduct any current to or from the tissue. This ensures that inactive electrodes do not interfere with the character of the signal transmitted to the skin.

The device may also include a signal generator or voltage control unit 18. The voltage control 18 may be adapted to modulate a frequency of the voltage provided by the power supply 12 and to the positive electrodes. Furthermore, the voltage control 18 may also be adapted to provide a wide range of other features, such as modulating the amplitude, pulse rate, pulse sweep, and duty cycle of the voltage provided by the power supply. This provides for fine control of the stimulation of the tissue by providing the means to control the specific pattern and signal characteristics of the signal. The voltage control 18 may provide the signal to an amplification and distribution unit 20. The amplification and distribution unit may amplify the signal and provide the proper circuitry for selectively configuring the nodes between possible states. The circuitry may include solid state switching to control the configuration of the nodes 16. The voltage control unit 18 may be separate from the applicator 14 and instead integrated with the power supply 12 into a base unit. Alternatively, the voltage control 18 may be integrated into the applicator 14.

While at least one positive electrode may be used to conduct current to the skin, a negative electrode does not need to be provided to return current. Instead, if all negative electrodes are configured to be electrically isolated, the current can be dissipated through the skin. During this dissipation period, the positive electrodes may also be electrically isolated, allowing for a period where no energy is delivered to the skin. In such a way, the tissue can be provided with a "rest period" to be allowed to return to its natural electrical condition. Nodes can also be selectively disabled to provide different patterns of contact with the skin. Additionally, the voltage control unit 18 may be used to generate periodic or intermittent positive voltage to be delivered to the tissue and then cease generating during a negative phase of the signal. In such a manner, the voltage control unit 18 can supply the periodic "rest" pattern independent of the node configuration. This allows for flexible methods to provide additional stimulation to the tissue.

Figure 2:
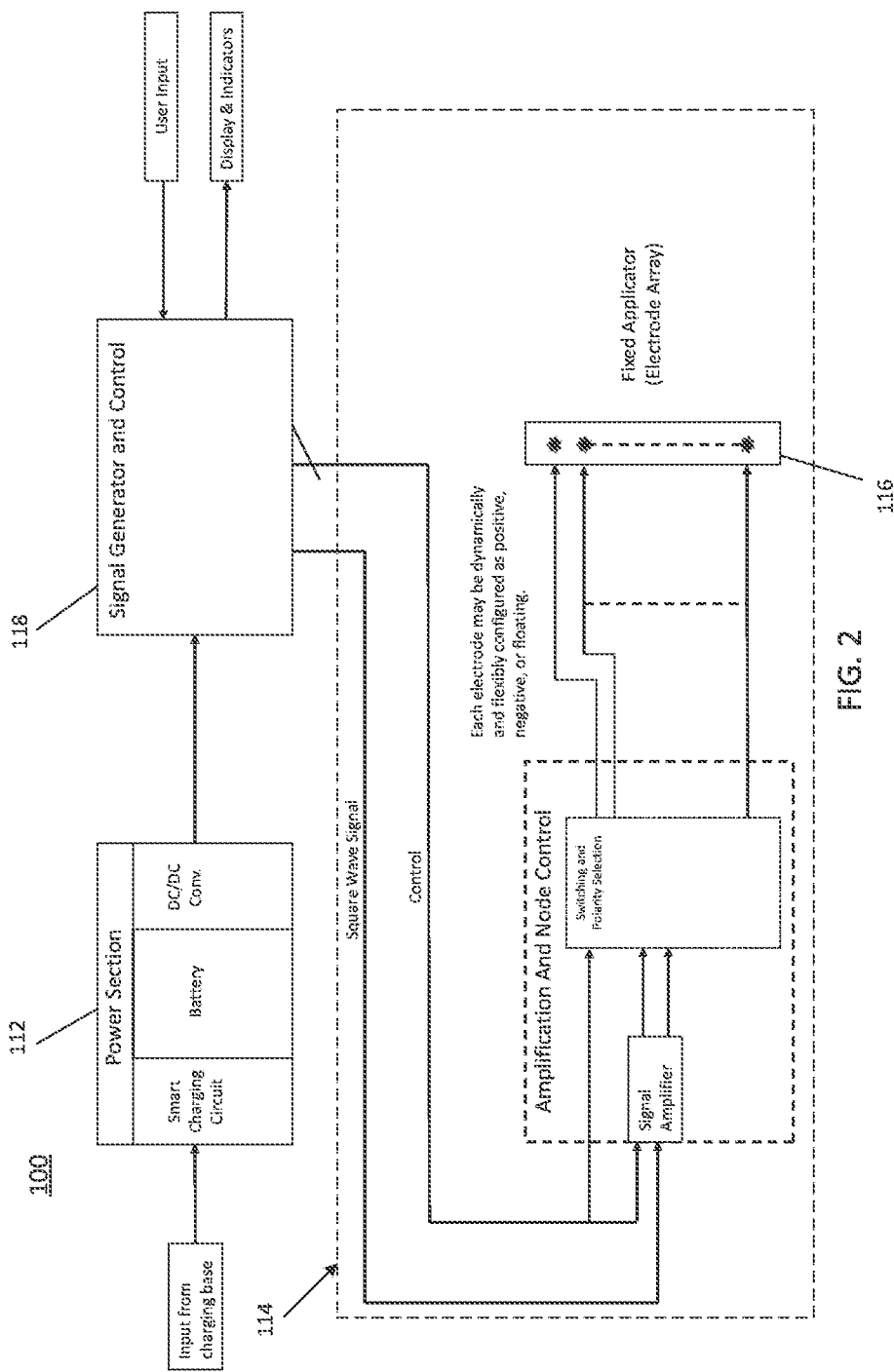
FIG. 2 is a block diagram of a skin rejuvenation device according to an embodiment of the invention.

In another aspect of the invention, each node instead may be selectively configurable between three states: a positive electrode, a negative electrode, and floating. This aspect provides for complex and dynamic patterns of tissue stimulation. For example, patterns such as linear, circular, or spiral "waves" may be applied and this may optimize the treatment of a broad range of skin conditions. As shown in FIG. 2, the device 100 includes power supply 112. The device 100 also includes nodes 116 on applicator 114 that may be dynamically and flexibly configured as positive, negative, or floating. The configuration of the nodes 116 are controlled by the voltage control unit 118. The voltage control unit 118 may control the signal in a manner similar to the control unit 18, but accounts for the three possible states of each node.

Figure 3:
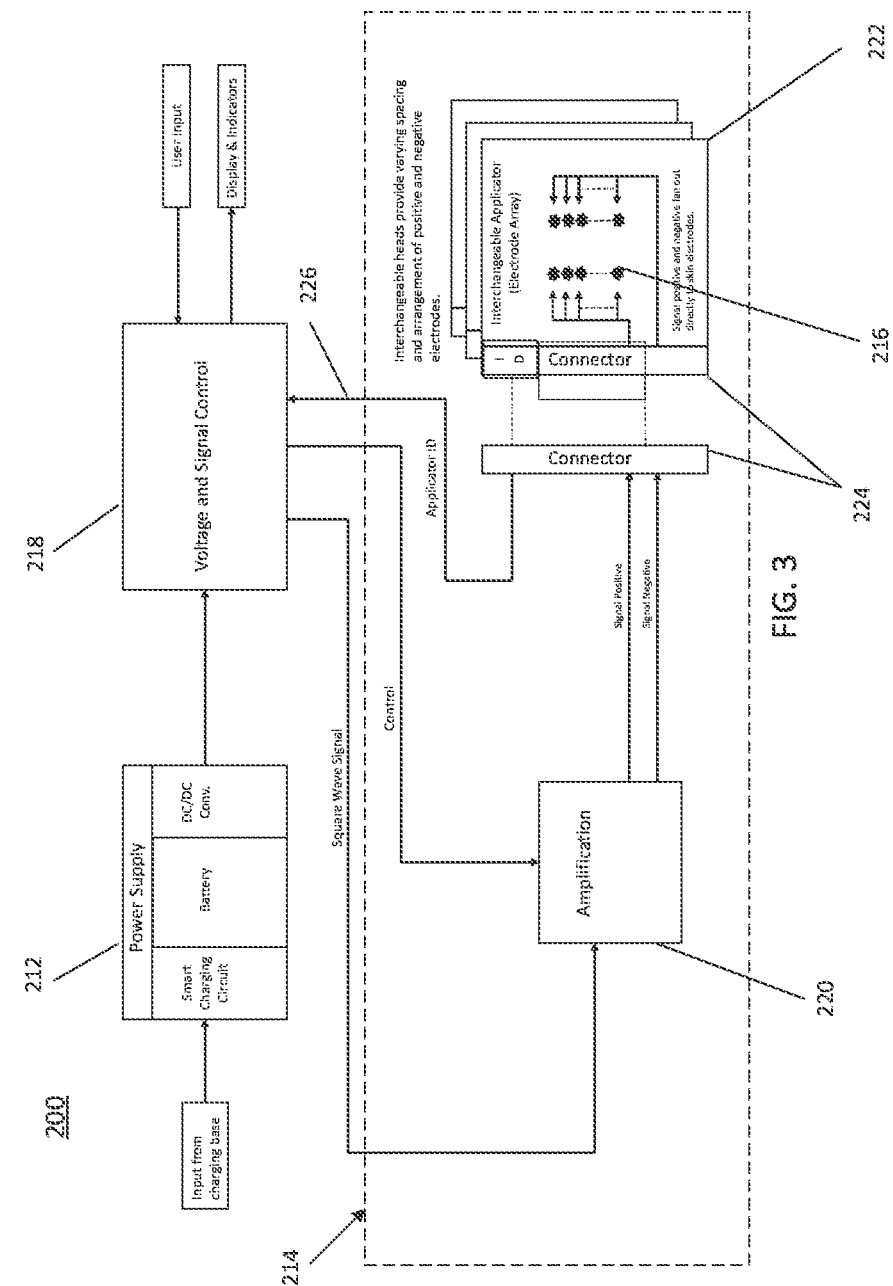
FIG. 3 is a block diagram of a skin rejuvenation device according to an embodiment of the invention.

Referring now to FIG. 3, in another aspect of the invention, the device 200 includes an applicator 214 that may be adapted to have a detachable applicator head 222. Each applicator head 222 may have a distinct pattern of positive and negative electrodes 216 to apply stimulation to tissue. By exchanging different applicator heads 222, the device may provide varying patterns without including the switching and other circuitry in the applicator 214. The applicator 214 may couple with the applicator head 222 with a connector 224 that provides the positive and negative path for the stimulation signal. The applicator head 222 may also provide a separate identification signal 226 to the voltage control 218. In this way, the voltage control 218 can identify the specific applicator head 222 currently attached to the applicator 214 and adjust the signal accordingly. The voltage control unit 218 may provide similar functionality as in the other aspects of the invention.

In each aspect of the invention, the device may include a means to update or change the software or operation of the device. For example, operation of the voltage control unit may be updated, including the frequency or voltage of the signal supplied to skin or other tissue. The pattern of node activation may also be configured. The device may be updated through a physical connection, such as USB, or through a wireless connection, such as WiFi or Bluetooth. Each aspect of the invention may be a hand-held device. Alternatively, the applicator may be separate from a base containing the power supply and voltage control unit and electrically coupled via a cord or wire.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A skin rejuvenation device, the device comprising:
   a power supply adapted to generate a voltage and having at least two output terminals, said power supply providing a positive polarity between one of said at least two output terminals and ground and a negative polarity between another of said at least two terminals and ground;
   an applicator comprising a first node and a second node, said first and second nodes adapted to come into contact with the skin to be treated, wherein said applicator comprises an array of said first nodes and said second nodes and is adapted to be operated by a user to move said array of said first nodes and said second nodes over the skin to be treated; and
   a control, wherein said control is adapted to periodically connect the first nodes between a positive one of said at least two terminals or electrically isolated from the power supply in order to float with respect to ground, and wherein said control is adapted to periodically connect the second nodes between a negative one of said at least two terminals or electrically isolated from the power supply in order to float with respect to ground; and
   wherein the power supply delivers a current through the first nodes when the control connects the first nodes to the positive one of said at least two terminals and current returns to the power supply through the second nodes when the control connects the second nodes to be the negative one of said at least two terminals and wherein the control is adapted to fully electrically isolate the skin so that no current is delivered to or from the skin when said control isolates said two nodes from the power supply to define a dissipation period during which first and second nodes are electrically floating wherein current is dissipated through the skin sufficient to return the skin to its natural electrical condition.

2. The device of claim 1, further comprising a voltage control adapted to modulate a frequency of the voltage.

3. The device of claim 2, wherein the voltage control is further adapted to modulate the frequency of the voltage between 1,000 Hz and 350,000 Hz.

4. The device of claim 2, wherein the voltage control is further adapted to modulate at least one selected from an amplitude, pulse rate, pulse sweep, and duty cycle of the voltage.

5. The device of claim 2, wherein the device further comprises a network interface.

6. The device of claim 2, wherein the device further comprises a wireless interface.

7. The device of claim 1, wherein the applicator further comprises a convex surface, wherein the first nodes and the second nodes are disposed on the convex surface.

8. The device of claim 1, wherein the power supply is adapted to deliver a periodic voltage comprising of a first period of positive voltage through the first node followed by a second period of no voltage through the first node.

9. The device of claim 1 wherein said device is adapted to deliver no more than 1 milliampere of current to the skin to be treated.

10. A skin rejuvenation device, the device comprising:
a power supply adapted to generate a voltage and having at least two output terminals, said power supply providing a particular polarity between one of said at least two output terminals and ground;
an applicator comprising a plurality of spaced apart electrically conductive nodes said conductive nodes adapted to come into contact with the skin to be treated; and
a control, wherein said control is adapted to selectively connect each of said nodes with one of said output terminals, the other of said output terminals or to float with respect to ground, wherein said plurality of said nodes comprise a plurality of first nodes, a plurality of second nodes, and a plurality of third nodes, wherein at least some of said third nodes are between one of said first nodes and said one of said second nodes, wherein said applicator comprises an array of said first nodes said second nodes and said third nodes and is adapted to be operated by a user to move said array of said first nodes said second nodes and said third nodes over the skin to be treated, wherein said control is adapted to selectively define a plurality of patterns of connection of said nodes with said at least two output terminals, with, a first of said patterns selectively connecting said first nodes with one of said at least two output terminals, said second nodes with said other of said at least two output terminals and said third nodes to float with respect to ground wherein the control is adapted to fully electrically isolate the skin so that no current is delivered to or from the skin when said control isolates said third nodes from the power supply to define a dissipation period during which said third nodes are electrically floating wherein current is dissipated through the skin sufficient to return the skin to its natural electrical condition, wherein said plurality of patterns comprising at least one chosen from linear waves, circular waves or spiral waves in order to treat multiple different skin conditions.

11. The device as claimed in claim 10, wherein said control applies said output to at least one of said nodes to activate that node and not to at least one other node to allow that other node to float.

12. The device as claimed in claim 10 wherein said control applies said output to at least one of said nodes to activate that node and allows that node to float to discharge that node.

13. The device as claimed in claim 10, wherein said control is adapted to connect alternating ones of said electrodes with said one output terminal and said second output terminal to define a second pattern wherein all of said nodes are activated.

14. The device of claim 10, further comprising a voltage control adapted to modulate a frequency of the voltage.

15. The device of claim 14, wherein the voltage control is adapted to modulate the frequency of the voltage between 1,000 Hz and 350,000 Hz.

16. The device of claim 10, wherein the power supply is adapted to deliver a periodic voltage comprising of a first period positive voltage through at least one output terminal followed by a second period of no voltage through any of the output terminals.

17. The device of claim 10 wherein said device is adapted to deliver no more than 1 milliampere of current to the skin to be treated.

18. A method for rejuvenating skin with a device, the device having a power supply adapted to generate a voltage and an applicator, said power supply having at least two output terminals and providing a positive polarity between one of said at least two output terminals and ground and a negative polarity between another of said at least two terminals and ground, said applicator have a first node and a second node, and causing said first and second nodes to come into contact with the skin to be treated, the method comprising:
configuring the first node as a positive electrode electrically coupled to the one of said at least two output terminals the power supply or electrically isolated from the power supply, and configuring the second node as a negative electrode coupled to the another of said at least two terminals of the power supply or electrically isolated from the power supply; and
periodically delivering a current with the power supply through the first node to the skin when the first node is configured as the positive electrode and periodically returning a current from the skin to the power supply through the second node when the second node is configured to be the negative electrode and fully electrically isolating the skin thereby allowing the skin to return to its natural electrical condition by said first and second nodes being electrically floating thereby delivering no current to or from the skin when the first and second nodes are isolated from the power supply to define a dissipation period during which current is dissipated through the skin; and
wherein said applicator comprises an array of said first nodes and said second nodes and wherein said causing said first and said second nodes to come into contact with the skin to be treated includes moving the array of said first nodes and said second nodes over the skin.

19. The method as claimed in claim 18 including delivering no more than 1 milliampere to the skin to be treated.

* * * * *

UNITED STATES PATENT AND TRADEMARK OFFICE
CERTIFICATE OF CORRECTION

PATENT NO. : 11,420,048 B2
APPLICATION NO. : 16/643382
DATED : August 23, 2022
INVENTOR(S) : Mark Campbell and Thomas Murphy It is certified that error appears in the above-identified patent and that said Letters Patent is hereby corrected as shown below:

In the Claims

Column 6
Line 52, Claim 1, insert --said-- after --which--

Signed and Sealed this
Thirteenth Day of June, 2023

Katherine Kelly Vidal
*Director of the United States Patent and Trademark Office*